(12) United States Patent
Bogaki et al.

(10) Patent No.: US 9,947,162 B2
(45) Date of Patent: Apr. 17, 2018

(54) IMAGE ACQUISITION DEVICE AND IMAGE ACQUISITION METHOD

(71) Applicant: GLORY LTD., Himeji-shi, Hyogo (JP)

(72) Inventors: Akira Bogaki, Himeji (JP); Takahiro Yanagiuchi, Himeji (JP); Takaaki Morimoto, Himeji (JP); Satoru Oshima, Himeji (JP)

(73) Assignee: GLORY LTD., Himeji-shi, Hyogo (JP)

( * ) Notice: Subject to any disclaimer, the term of this patent is extended or adjusted under 35 U.S.C. 154(b) by 214 days.

(21) Appl. No.: 14/787,048

(22) PCT Filed: Apr. 30, 2013

(86) PCT No.: PCT/JP2013/062666
§ 371 (c)(1),
(2) Date: Oct. 26, 2015

(87) PCT Pub. No.: WO2014/178129
PCT Pub. Date: Nov. 6, 2014

(65) Prior Publication Data
US 2016/0070947 A1    Mar. 10, 2016

(51) Int. Cl.
*G07D 7/12* (2016.01)
*G01N 21/55* (2014.01)
(Continued)

(52) U.S. Cl.
CPC ............. *G07D 7/121* (2013.01); *G01N 21/55* (2013.01); *G01N 21/59* (2013.01); *G07D 7/12* (2013.01);
(Continued)

(58) Field of Classification Search
CPC ................... G01N 21/55; G01N 21/59; G01N 2201/0633; G01N 2201/061; G07D 7/12; G07D 7/121
(Continued)

(56) References Cited

U.S. PATENT DOCUMENTS 5,650,863 A * 7/1997 Utagawa .............. G03G 21/046
358/475
2002/0015145 A1    2/2002 Numata
(Continued)

FOREIGN PATENT DOCUMENTS

EP    1 752 933 A2    2/2007
EP    2 211 312 A2    7/2010
(Continued)

OTHER PUBLICATIONS

European Search Report (Application No. 13883595.4—PCT/JP2013062666) (8 pages dated Jul. 11, 2016).
(Continued)

*Primary Examiner* — Hina F Ayub
*Assistant Examiner* — Amanda Merlino
(74) *Attorney, Agent, or Firm* — Renner, Kenner, Greive, Bobak, Taylor & Weber

(57) ABSTRACT

Light is emitted on one side of a paper sheet 100, which is being transported on a transport path, from a first light source 11, and light is emitted on other side of the paper sheet 100 from a second light source 21 and a fourth light source 22. A first light receiving sensor 14 receives a first reflected light, which is the light emitted by the first light source 11 and reflected from the one side of the paper sheet 100. A second light receiving sensor 24 receives a second reflected light, which is the light emitted by the second light source 21 and the fourth light source 22 and reflected from the other side of the paper sheet 100, and receives a transmitted light that is the light emitted by the first light source 11 and that has passed through the paper sheet 100.

11 Claims, 9 Drawing Sheets

(51) Int. Cl.
*G01N 21/59* (2006.01)
*G07D 7/121* (2016.01)
*G06K 9/00* (2006.01)

(52) U.S. Cl.
CPC ............... *G01N 2201/061* (2013.01); *G01N 2201/0633* (2013.01); *G06K 9/00013* (2013.01)

(58) Field of Classification Search
USPC .......................................................... 356/71
See application file for complete search history.

(56) References Cited

U.S. PATENT DOCUMENTS

| | | |
|---|---|---|
| 2004/0164248 A1 | 8/2004 | Nago et al. |
| 2004/0240721 A1 | 12/2004 | Tsuji et al. |
| 2009/0003784 A1 | 1/2009 | Kabuki et al. |
| 2009/0109500 A1 | 4/2009 | Hasegawa et al. |
| 2015/0249104 A1 | 9/2015 | Ota et al. |
| 2015/0316706 A1 | 11/2015 | Fujiuchi et al. |

FOREIGN PATENT DOCUMENTS

| | | |
|---|---|---|
| EP | 2 911 379 A1 | 8/2015 |
| JP | 2001-320551 A | 11/2001 |
| JP | 2002-190916 A | 7/2002 |
| JP | 2007-141109 A | 6/2007 |
| JP | 4334912 B2 | 7/2009 |
| JP | 4334913 B2 | 7/2009 |
| JP | 2010-212799 A | 9/2010 |

OTHER PUBLICATIONS

Japanese Office Action (Application No. 2015-514723) (2 pages—dated Aug. 23, 2016).
Japanese Office Action (Application No. 2015-514723) (16 pages—dated Oct. 11, 2017).

* cited by examiner

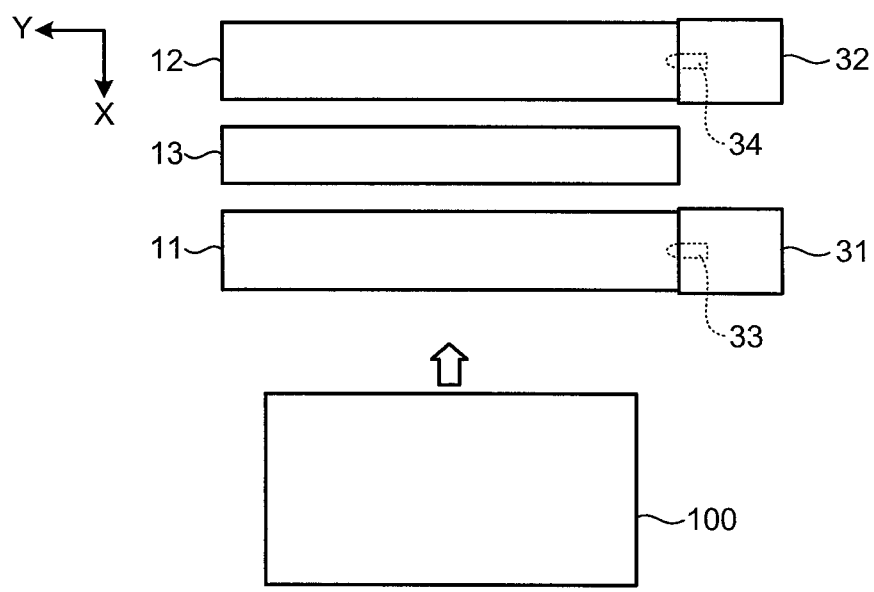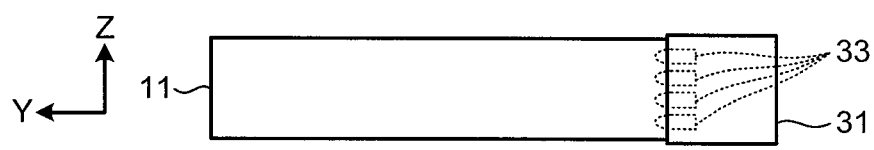

FIG.4
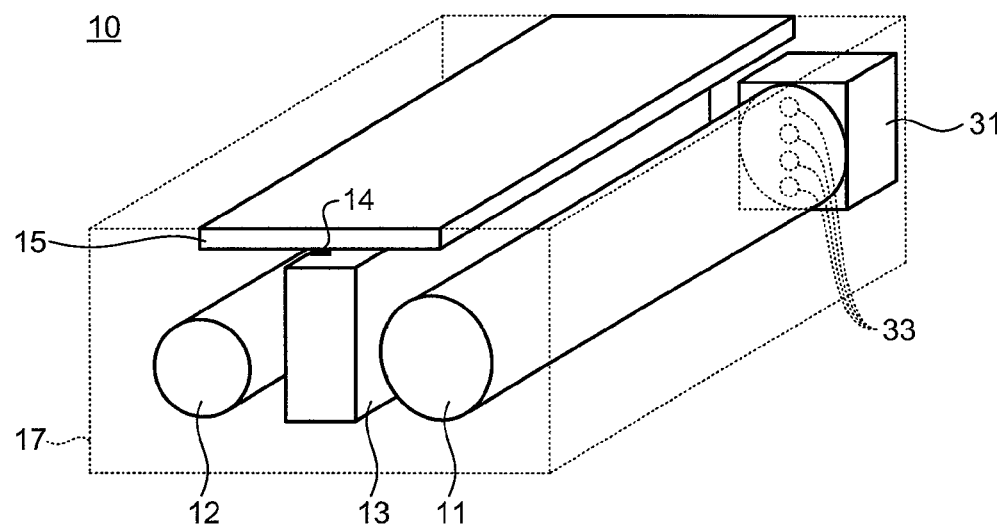
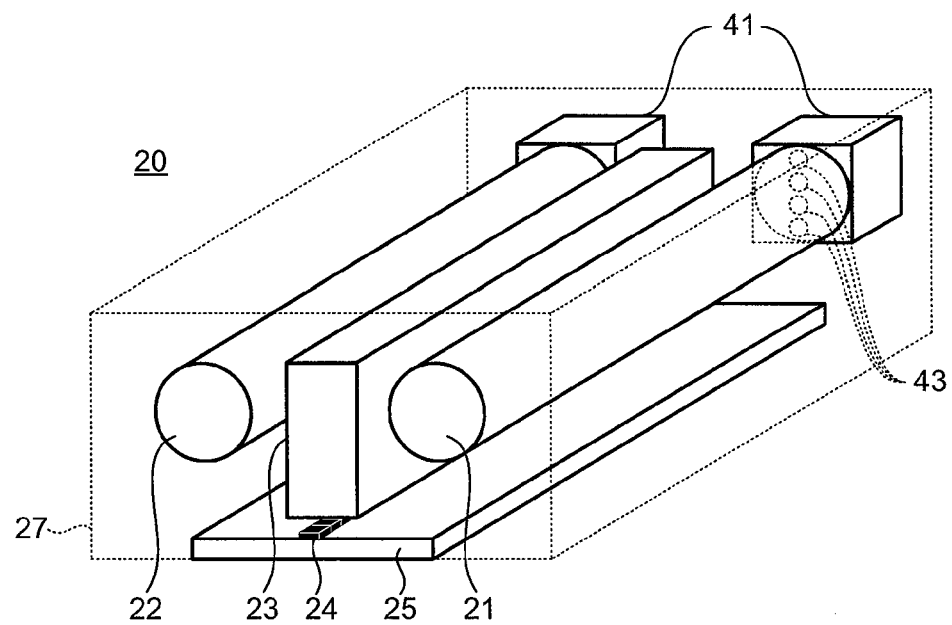

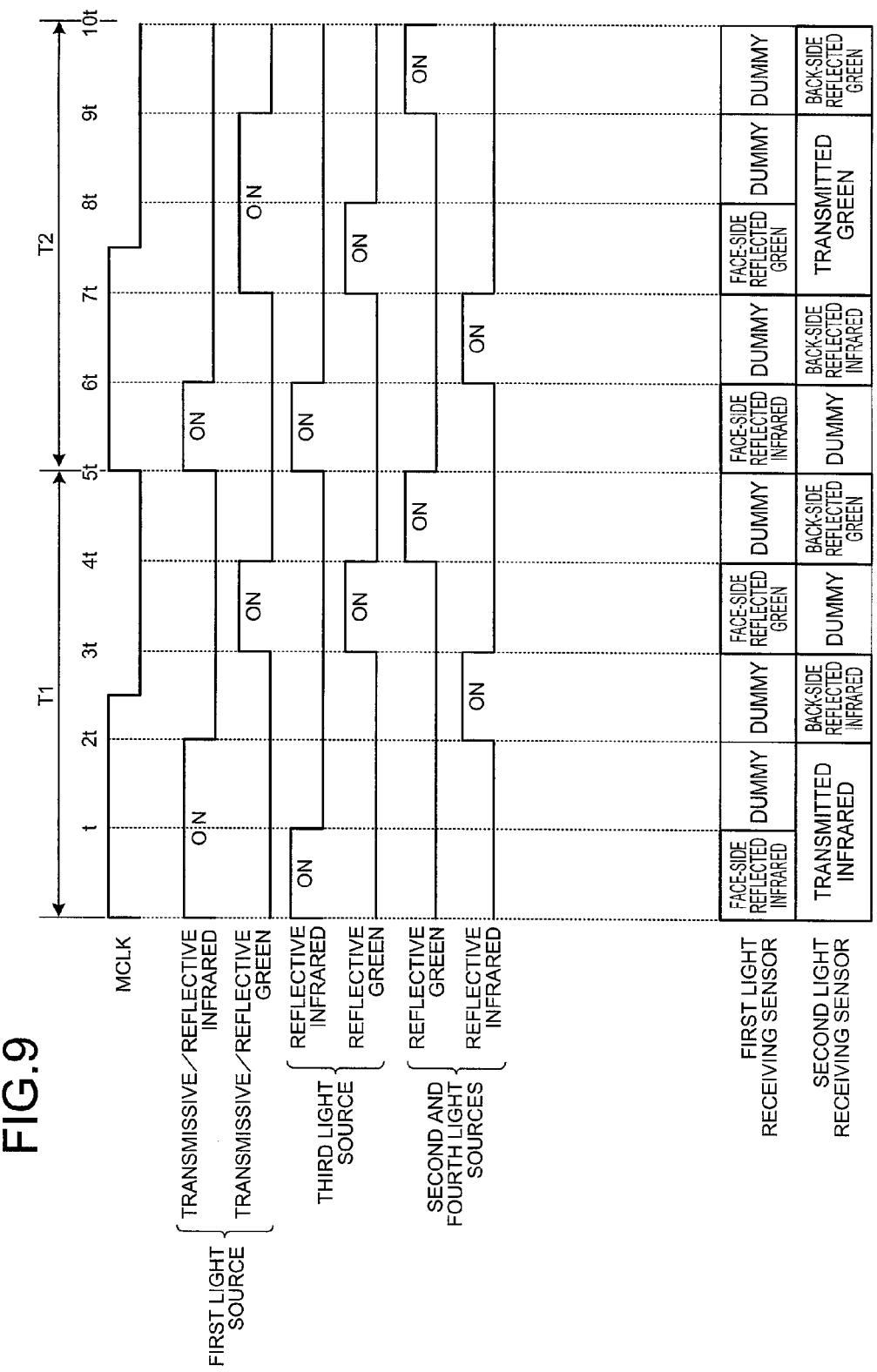

IMAGE ACQUISITION DEVICE AND IMAGE ACQUISITION METHOD

TECHNICAL FIELD

The present invention relates to an image acquisition device and an image acquisition method that acquire image data of a paper sheet that is being transported on a transport path.

BACKGROUND ART

Devices that acquire image data by capturing a paper sheet to perform recognition of a kind and an authentication of the paper sheet, management of the paper sheet, and the like, are known in the art. Patent Document 1, for example, discloses a banknote processing machine that acquires image data of a banknote by capturing the banknote, and recognizes a kind and an authentication of the banknote based on characteristic features obtained from the image data. Specifically, in the banknote processing machine disclosed in Patent Document 1, a light guiding plate is arranged above the banknote, light is emitted on the banknote from a light source arranged on a side of the light guiding plate, a reflection image of the banknote is acquired by receiving light reflected from the banknote in a first sensor. The first sensor is arranged above the banknote, similarly to the light guiding plate. Additionally, a transmission image of the banknote is acquired by receiving light that has passed through the banknote in a second sensor that is arranged below the banknote. In this banknote processing machine, by sequentially turning on light sources of a plurality of wavelengths, an image corresponding to each of the wavelengths can be captured.

The banknote processing machine disclosed in Patent Document 1 can acquire a transmission image and a reflection image of one side of the banknote; however, to recognize a kind and an authentication of the banknote, it is desirable to read reflection images of the both sides of the banknotes to obtain characteristic features of each side of the banknotes. Devices that acquire a transmission image and reflection images of both sides of banknotes are known in the art. In the banknote image detection devices disclosed in Patent Document 2 and Patent Document 3, for example, one detecting unit is arranged above and another detecting unit is arranged below the banknote, each detecting unit includes a light source and an image detecting sensor, thereby acquiring a transmission image and reflection images of both sides of the banknote. In the device of Patent Document 2 and the device of Patent Document 3, the positional arrangement of the light source and the image detecting sensor in the detecting unit is different.

CITATION LIST

Patent Document

[Patent Document 1] Japanese Patent Application Laid-open No. 2001-357429
[Patent Document 2] Japanese Patent 4334913
[Patent Document 3] Japanese Patent 4334912

SUMMARY OF INVENTION

Technical Problem

However, satisfactory image data may not be acquired even by using the conventional technique. Specifically, in the device disclosed in Patent Document 2, because the light source and the sensor, which are used for capturing the transmission image, are arranged at shifted positions, it is difficult to obtain a satisfactory transmission image due to insufficient transmitted light quantity.

In the device disclosed in Patent Document 3, a light source and a sensor, which are used for capturing the transmission image, are arranged at positions facing each other; however, because a light source used for acquiring the reflection image is installed only on one side with respect to a fiber lens array, it is difficult to obtain a satisfactory reflection image. Moreover, this device has a configuration where one transmission image is obtained from light that passes the banknote from above to below and another transmission image is obtained from light that passes the banknote from below to above; however, it is sufficient to obtain one transmission image so that the device has an excess light source.

In order to obtain a satisfactory image of a banknote, it is desirable to take into account a directivity of the light and emitting enough quantity of light toward the banknote. Moreover, the image acquisition device is used inside a banknote processing apparatus and the like; and in recent years, there has been a requirement of cost reduction and downsizing of the banknote processing apparatus. That is, there is a requirement that the image acquisition device be able to obtain a satisfactory image while being small and low-cost.

The present invention has been devised to solve the above-explained issues in the conventional techniques. It is an object of the present invention to provide an image acquisition device and an image acquisition method capable of acquiring a satisfactory reflection image and a satisfactory transmission image while realizing downsizing of the device.

Means For Solving Problems

To solve the above issues and to achieve the above objects, according to one aspect of the present invention, an image acquisition device that acquires image data of a paper sheet being transported on a transport path includes a first light source arranged on one side of the paper sheet being transported on the transport path; a first light receiving sensor that receives a reflected light that is emitted by the first light source and reflected from the paper sheet being transported; and a second light receiving sensor arranged on other side of the paper sheet being transported on the transport path and that receives a transmitted light that has passed through the paper sheet being transported, wherein the first light source outputs a light having directivity in both directions of a first direction from where the reflected light reflected from the paper sheet being transported is supplied to the first light receiving sensor and a second direction from where the transmitted light is supplied to the second light receiving sensor.

The above image acquisition device further includes a second light source arranged on the other side on which the second light receiving sensor is arranged, wherein the first light receiving sensor receives a first reflected light that is emitted by the first light source and reflected from the one side of the paper sheet, and the second light receiving sensor receives a second reflected light that is emitted by the second light source and reflected from the other side of the paper sheet, and receives the transmitted light that is emitted by the first light source and that has passed through the paper sheet.

The above image acquisition device further includes a third light source arranged on the same side as the first light receiving sensor, at a position where front back positional relation between the first light source and the first light receiving sensor is reversed; and a second light source and a fourth light source arranged on the same side as the second light receiving sensor, being arranged in each of front and back of the second light receiving sensor.

In the above image acquisition device, the first light source is a line-shaped light source that emits a predetermined light quantity by dividing in the first direction and the second direction, and a division ratio of the light quantity to be emitted in the second direction is higher than a division ratio of the light quantity to be emitted in the first direction.

In the above image acquisition device, an accumulation time for accumulating optical charge in the second light receiving sensor when receiving the transmitted light is longer than one or both of an accumulation time for accumulating optical charge in the first light receiving sensor when receiving the reflected light reflected from the paper sheet being transported and an accumulation time for accumulating optical charge in the second light receiving sensor when receiving the reflected light reflected from the paper sheet being transported.

In the above image acquisition device, a lighting time of the first light source when the second light receiving sensor receives the transmitted light is longer than one or both of a lighting time of the first light source when the first light receiving sensor receives the reflected light reflected from the paper sheet being transported and a lighting time of the second light source when the second light receiving sensor receives the reflected light reflected from the paper sheet being transported.

In the above image acquisition device, a light emission current supplied to the first light source when the second light receiving sensor receives the transmitted light is larger than one or both of a light emission current supplied to the first light source when the first light receiving sensor receives the reflected light reflected from the paper sheet being transported and a light emission current supplied to the second light source when the second light receiving sensor receives the reflected light reflected from the paper sheet being transported.

In the above image acquisition device, an amplification factor by which an output of the second light receiving sensor is amplified when the second light receiving sensor receives the transmitted light is higher than one or both of an amplification factor by which an output of the first light receiving sensor is amplified when the first light receiving sensor receives the reflected light reflected from the paper sheet being transported and an amplification factor by which an output of the second light receiving sensor is amplified when the second light receiving sensor receives the reflected light reflected from the paper sheet being transported.

In the above image acquisition device, light reception by the first light receiving sensor of the reflected light from the paper sheet being transported and light reception by the second light receiving sensor of the transmitted light are performed simultaneously.

In the above image acquisition device, one or both of the first light source and the second light source performs light emission of different wavelengths in a time division manner, and at least one among a lighting time of one or both of the first light source and the second light source, a light emission current to be supplied to one or both of the first light source and the second light source, an accumulation time of the first light receiving sensor and the second light receiving sensor, and an amplification factor for amplifying an output of the first light receiving sensor and the second light receiving sensor, are changed based on the wavelength.

According to another aspect of the present invention, an image acquisition method of acquiring image data of a paper sheet being transported on a transport path includes a first emission step in which a first light source, arranged on one side of the paper sheet being transported on the transport path, emits a light having a directivity in both directions of a first direction from where a light reflected from one side of the paper sheet is received by a first light receiving sensor and a second direction from where a transmitted light that has passed through the paper sheet is received by a second light receiving sensor arranged on other side of the transport path; a first reflected light receiving step in which the first light receiving sensor receives a first reflected light emitted by the first light source and reflected from the one side of the paper sheet; and a transmitted light receiving step in which the second light receiving sensor receives a transmitted light emitted by the first light source and that has passed through the paper sheet.

Advantageous Effects of Invention

An image acquisition device includes a first light source arranged on one side of a paper sheet being transported on a transport path; a first light receiving sensor that receives a reflected light that has been emitted by the first light source and reflected from the paper sheet being transported; and a second light receiving sensor arranged on the other side of the paper sheet being transported on the transport path and that receives a transmitted light that has passed through the paper sheet being transported. The first light source outputs a light having directivity in both directions of a first direction and a second direction. The reflected light that is emitted in the first direction and reflected from the paper sheet being transported is received by the first light receiving sensor, and the transmitted light emitted in the second direction is received by the second light receiving sensor. Thus, satisfactory reflection image and transmission image of the paper sheet can be acquired while realizing the downsizing of the device.

BRIEF DESCRIPTION OF DRAWINGS

FIG. 2 is an explanatory diagram for explaining a positional relationship between an upper light receiving/emitting unit and a paper sheet.

FIG. 4 is a perspective view of the light receiving/emitting unit.

FIG. 9 is an explanatory diagram for explaining a concrete example of an operation of the image acquisition device when performing simultaneous acquisition.

DESCRIPTION OF EMBODIMENTS

Exemplary embodiments of an image acquisition device and an image acquisition method according to the present invention are explained below in detail while referring to the accompanying drawings. The image acquisition device according to the present embodiment has a function for generating an image of various paper sheets such as a check, a gift coupon, and valuable securities, and the like. For example, the image acquisition device is used in a paper-sheet processing apparatus. The paper-sheet processing apparatus recognizes a kind and an authentication of the paper sheet by extracting characteristic features from an image generated in the image acquisition device.

Embodiments

Figure 1:
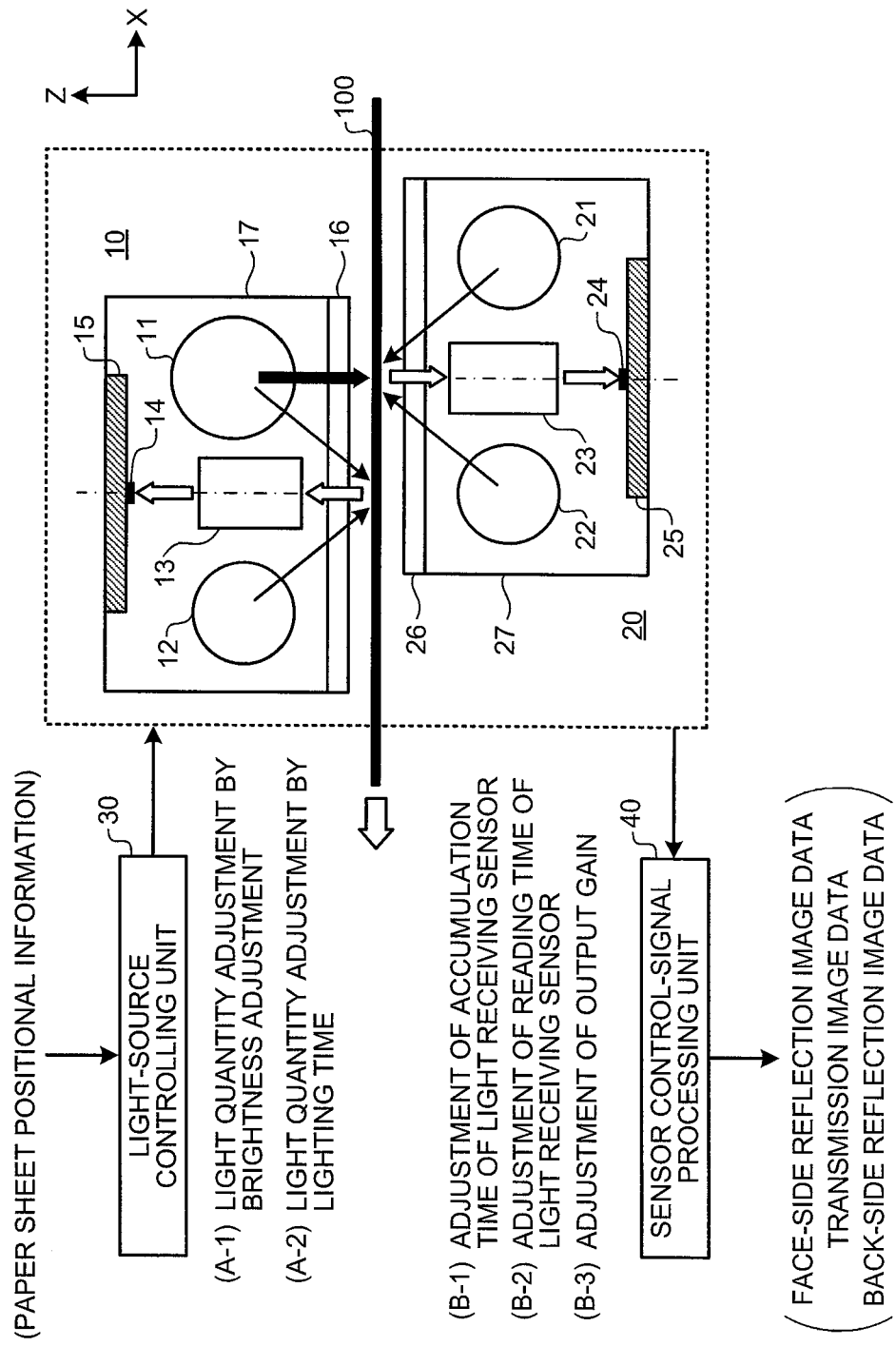
FIG. 1 is an explanatory diagram for explaining a concept of image acquisition according to an embodiment.

To begin with, a concept of image acquisition according to the present embodiment is explained. FIG. 1 is an explanatory diagram for explaining the concept of the image acquisition according to the embodiment. The image acquisition device according to the present embodiment includes a transport path for transporting a paper sheet 100. It is assumed herein that a transportation direction of the paper sheet 100 corresponds to a negative X-axis direction, an axis that is perpendicular to a surface of the paper sheet 100 is a Z-axis, and a Y-axis is perpendicular to the X-axis and the Z-axis. Moreover, it is assumed that the paper sheet 100 is transported substantially horizontally, and the positive side of the Z-axis will be called an upper side and the negative side of the Z-axis will be called a lower side. Furthermore, for the convenience of the explanation, the surface of the paper sheet 100 on the positive side of the Z-axis will be called a face side and the surface of the paper sheet 100 on the negative side of the Z-axis will be called a back side.

The image acquisition device includes two light receiving/emitting units 10 and 20. FIG. 1 shows a schematic cross-sectional view of the two light receiving/emitting units 10 and 20 when viewed from the Y-axis direction. As shown in FIG. 1, the light receiving/emitting units 10 and 20 face each other across a transport path.

The light receiving/emitting unit 10 is arranged on the positive side of the Z-axis direction, and a transparent member 16 made of glass or resin is fitted into a lower surface (surface facing the paper sheet 100) of a housing 17 thereof. The light receiving/emitting unit 10 includes a first light source 11 that emits light on the face side of the paper sheet 100. Moreover, the light receiving/emitting unit 10 includes a first light condenser lens 13 and a first substrate 15. A first light receiving sensor 14 is mounted on the first substrate 15. The first light receiving sensor 14 is arranged in a plural number along the Y-axis direction and constitutes an image line sensor.

The first light condenser lens 13 is arranged such that it condenses a reflected light, which is a light reflected from the face side of the paper sheet 100 when light is emitted by the first light source 11, and the condensed reflected light is received by the first light receiving sensor 14. Accordingly, face-side reflection image data of the paper sheet 100 can be generated by using the output signal of the first light receiving sensor 14.

Although the details will be explained later, a transmitted light, which is a light emitted by the first light source 11 and has passed through the paper sheet 100, is received by a second light receiving sensor 24 arranged inside the light receiving/emitting unit 20. The transmitted light is used for generating transmission image data of the paper sheet 100. In other words, the first light source 11 is used in common for the generation of the face-side reflection image data of the paper sheet 100 and the generation of the transmission image data of the paper sheet 100.

The light receiving/emitting unit 10 further includes a third light source 12 that emits light on the face side of the paper sheet 100. The light emitted by the third light source 12 is reflected from the face side of the paper sheet 100, condensed by the first light condenser lens 13, and received by the first light receiving sensor 14. The third light source 12 is for supplementing the light quantity of the first light source 11 when generating the face-side reflection image data of the paper sheet 100. That is, the third light source 12 does not contribute to the generation of the transmission image data.

The light receiving/emitting unit 20 is arranged on the negative side of the Z-axis direction. A transparent member 26 made of glass or resin is fitted into an upper surface (surface facing the paper sheet 100) of a housing of the light receiving/emitting unit 20. The light receiving/emitting unit 20 includes a second light source 21 and a fourth light source 22 that emit light on the back side of the paper sheet 100. The light receiving/emitting unit 20 includes a second light condenser lens 23 and a second substrate 25. The second light receiving sensor 24 is mounted on the second substrate 25. The second light receiving sensor 24 is arranged in a plural number along the Y-axis direction and constitutes an image line sensor.

The second light condenser lens 23 is arranged such that it condenses a reflected light, which is reflected from the back side of the paper sheet 100 when the paper sheet 100 is irradiated with the second light source 21 and the fourth light source 22. The second light condenser lens 23 directs the condensed reflected light so that the condensed reflected light is received by the second light receiving sensor 24. Accordingly, back-side reflection image data of the paper sheet 100 can be generated by using the output signal of the second light receiving sensor 24.

The second light condenser lens 23 is positioned to face the first light source 11 of the light receiving/emitting unit 10. The second light condenser lens 23 condenses the transmitted light, which is light emitted by the first light source 11 and passed through the paper sheet 100, and directs the condensed transmitted light so that the condensed transmitted light is received by the second light receiving sensor 24. Accordingly, the transmission image data of the paper sheet 100 can be generated by using the output signal of the second light receiving sensor 24.

A light-source controlling unit 30 controls lighting of the first light source 11, the second light source 21, the fourth light source 22, and the third light source 12 based on positional information of the paper sheet 100. A sensor control/signal processing unit 40 controls the first light receiving sensor 14 and the second light receiving sensor 24 to receive light, and generates the face-side reflection image data, the transmission image data, and the back-side reflection image data by using the output signals of the first light receiving sensor 14 and the second light receiving sensor 24.

In this manner, in the image acquisition device according to the present embodiment, the first light source 11 is used in common for the generation of the face-side reflection image data and the generation of the transmission image data, and the second light receiving sensor 24 is used in common for the generation of the back-side reflection image data and the generation of the transmission image data. Accordingly, the face-side reflection image data, the transmission image data, and the back-side reflection image data can be obtained with a small and low-cost device configuration.

Because the transmission image data is generated by the transmitted light which has passed through the paper sheet 100, a larger light quantity is necessary to generate the transmission image data as compared to the light quantity necessary to generate the face-side reflection image data or the back-side reflection image data.

Accordingly, in the image acquisition device according to the present embodiment, at least one among a brightness of the first light source 11, a lighting time of the first light source 11, an accumulation time in which optical charge is accumulated in the second light receiving sensor 24, and an amplification factor (gain) by which the output signal of the second light receiving sensor 24 is amplified, is controlled by taking into account the directivity of the first light source 11, and thus a light quantity necessary for the generation of satisfactory transmission image data can be acquired.

Specifically, a light guiding member having a directivity in two directions, the first direction and the second direction, is used as the first light source 11. The light in the first direction is reflected from the face side of the paper sheet 100 and received by the first light receiving sensor 14, and the light in the second direction passes through the paper sheet 100 and is received by the second light receiving sensor 24. The light guiding member has a configuration that allows it to distribute a predetermined light quantity to be emitted in the first direction and the second direction, and set a distribution ratio of the light quantity to be emitted in the second direction to be larger than a distribution ratio of the light quantity to be emitted in the first direction. By taking into account the directivity of the light guiding member, light quantity suitable for the generation of the transmission image data is adjusted. The reason for adjusting the light quantity in this manner is that attenuation of the transmitted light by the paper sheet 100 is higher than attenuation of the reflected light by the paper sheet 100.

When using the first light source 11 for the generation of the transmission image data, in comparison to a case where the first light source 11 is used only for the generation of the face-side reflection image data, the light-source controlling unit 30 provides control so that the brightness of the first light source 11 is higher, thereby adjusting the light quantity suitable for the generation of the transmission image data (A-1). Although the details about the adjustment of the brightness will be explained later, the adjustment of the brightness can be performed by changing an electric current to be used for emitting light from the first light source 11.

When using the first light source 11 for the generation of the transmission image data, in comparison to a case where the first light source 11 is used only for the generation of the face-side reflection image data, the light-source controlling unit 30 provides a control so that the lighting time of the first light source 11 is longer, thereby adjusting the light quantity suitable for the generation of the transmission image data (A-2).

When using the second light receiving sensor 24 for the generation of the transmission image data, in comparison to a case where the second light receiving sensor 24 is used for the generation of the back-side reflection image data, the sensor control/signal processing unit 40 provides a control so that the optical charge accumulation time in the second light receiving sensor 24 is longer, thereby adjusting the light quantity suitable for the generation of the transmission image data (B-1).

Detailed explanation of the control of the accumulation time will be omitted herefrom as the method disclosed in Japanese Patent Application Laid-open No. H6-189066 and the like can be used to perform this control. One preferable approach for the control of the accumulation time is to change the exposure time of a photo-diode array when the light receiving sensor receives light of a target wavelength. The Japanese Patent Application Laid-open No. H6-189066 discloses to change a time of the cycle to determine the exposure time; however, other techniques can be employed. For example, a signal that specifies the exposure time can be added, and an output of each photo-diode included in one line can be buffered and both reading from the buffer and the exposure are performed in parallel, thereby reading of pixels for one line is always performed at the same time.

When using the second light receiving sensor 24 for the generation of the transmission image data, in comparison to a case where the second light receiving sensor 24 is used for the generation of the back-side reflection image data, the sensor control/signal processing unit 40 provides a control so that the accumulating time in which the second light receiving sensor 24 receives the transmitted light is longer, thereby adjusting the light quantity suitable for the generation of the transmission image data (B-2).

When using the second light receiving sensor 24 for the generation of the transmission image data, in comparison to a case where the second light receiving sensor 24 is used for the generation of the back-side reflection image data, the sensor control/signal processing unit 40 provides a control so that the gain by which the output signal from the second light receiving sensor 24 is amplified is higher, thereby adjusting the light quantity suitable for the generation of the transmission image data (B-3).

In the image acquisition device according to the present embodiment, in this manner, the face-side reflection image data, the transmission image data, and the back-side reflection image data can be suitably acquired by using the configuration and the control explained in (A-1) to (A-2) and (B-1) to (B-3) independently or in combination.

Next, the structure of the light receiving/emitting units 10 and 20 will be explained. FIG. 2 is an explanatory diagram for explaining a positional relationship between the upper light receiving/emitting unit 10 and the paper sheet 100. Specifically, FIG. 2A is a top view when the first light source 11, the third light source 12, and the first light condenser lens 13 of the light receiving/emitting unit 10 are viewed from the positive side of the Z-axis, and FIG. 2B is a front view when the first light source 11 of the light receiving/emitting unit 10 is viewed from the positive side of the X-axis. FIG. 3 is a modification example of the configuration of the light receiving/emitting units, and FIG. 4 is the perspective view of the light receiving/emitting units 10 and 20.

As shown in FIG. 2A, in the light receiving/emitting unit 10, the first light source 11, the first light condenser lens 13, and the third light source 12 are configured with a light guiding member that extends in the Y-axis direction. Accordingly, the first light source 11 and the third light source 12 can emit light on the entire width of the paper sheet 100 in the Y-axis direction when the paper sheet 100 passes below those light sources. Similarly, the first light condenser lens 13 can condense light from the entire width of the paper sheet 100 in the Y-axis direction when the paper sheet 100 passes below the condenser lens. The first light source 11, the first light condenser lens 13, and the third light source 12 are arranged such that the paper sheet 100 passes below the first light source 11 first, then passes below the first light condenser lens 13, and passes below the third light source 12 after that.

A light emitting unit 31 is arranged on one side of the first light source 11 and a light emitting unit 32 is arranged on one side of the third light source 12. The light emitting unit 31 includes four light emitting elements 33 and the light emitting unit 32 includes four light emitting elements 34. When the light emitting elements 33 and 34 are turned on, light enters into the first light source 11 and the third light source 12 from the side of the light guiding members. Although omitted from FIG. 2, with respect to the second light source 21 and the fourth light source 22 that are included in the light receiving/emitting unit 20, as shown in FIG. 4, by turning on the light emitting elements 43 included in light emitting units 41, light is caused to enter from a side thereof.

Figure 3A:
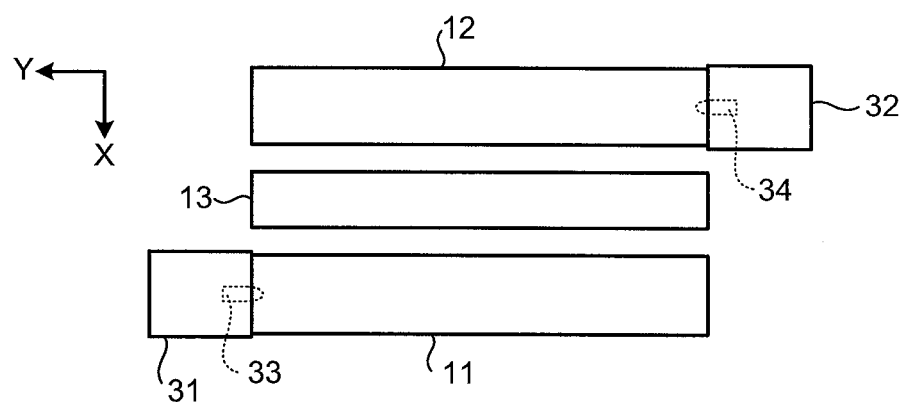
FIG. 3 is an explanatory diagram for explaining a modification example of a configuration of the light receiving/emitting unit.
Figure 3B:
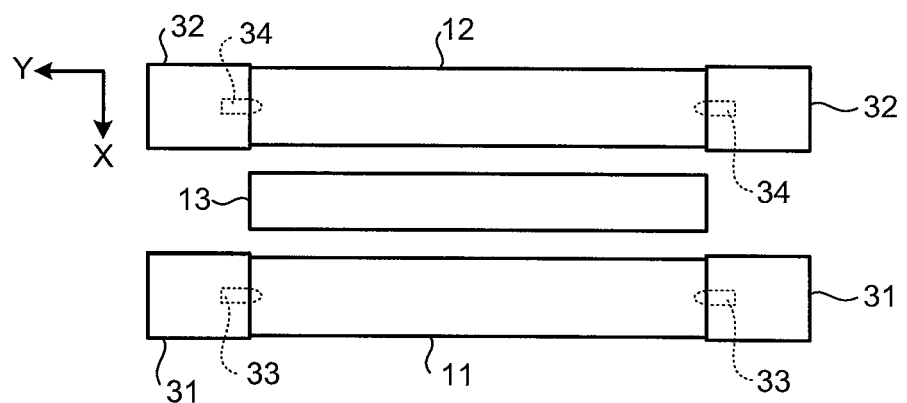

A configuration is shown in FIG. 2 in which the light emitting unit 31 and the light emitting unit 32 are arranged on the same side (the negative side of the Y-axis direction); however, as shown in FIG. 3A, the light emitting unit 31 and the light emitting unit 32 can be arranged on different sides. FIG. 3A shows a configuration in which the light emitting unit 31 is arranged on the positive side of the Y-axis direction of the first light source 11 and the light emitting unit 32 is arranged on the negative side of the Y-axis direction of the third light source 12. Alternatively, as shown in FIG. 3B, the light emitting units 31 and 32 can be arranged on both the sides (the positive side of the Y-axis direction and the negative side of the Y-axis direction) of the first light source 11 and the third light source 12, respectively.

In order to irradiate the paper sheet 100 with light of wavelengths necessary to acquire various image data, for example, LEDs (Light Emitting Diodes) each of which emits a light of a predetermined wavelength are employed as the light emitting elements 33, 34, and 43 used in the light emitting units 31, 32, and 41.

When lights of two wavelengths, infrared light and green visible light, are to be used, the four LEDs consisting of two LEDs that emit the infrared light and two LEDs that emit the green visible light can be used as the light emitting elements 33, 34 and 43.

Out of the light emitting elements 33 and 34, if the two LEDs of the infrared light are turned on, the infrared light is emitted on the face side of the paper sheet 100 from the first light source 11 and the third light source 12, and face-side reflection image data for the infrared light can be obtained. Because the first light source 11 can also be used as the light source for the transmission image data, when the two LEDs of the infrared light in the light emitting element 33 are turned on, transmission image data for the infrared light can be obtained.

Similarly, out of the light emitting elements 33 and 34, if the two LEDs of the green visible light are turned on, the green visible light is emitted on the face side of the paper sheet 100 from the first light source 11 and the third light source 12, and face-side reflection image data for the green visible light can be obtained. Also, when the two LEDs of the green visible light in the light emitting element 33 are turned on, transmission image data for the green visible light can be obtained.

Out of the light emitting elements 43, if the two LEDs of the infrared light are turned on, the infrared light is emitted on the back side of the paper sheet 100 from the second light source 21 and the fourth light source 22, and back-side reflection image data for the infrared light can be obtained. Similarly, out of the light emitting elements 43, if the two LEDs of the green visible light are turned on, the green visible light is emitted on the back side of the paper sheet 100 from the second light source 21 and the fourth light source 22, and back-side reflection image data for the green visible light can be obtained.

An exemplary configuration is shown here in which a plurality of elements each of which emits different wavelength light are included in the light emitting elements 33, 34, and 43; however, if one element can emit lights of different wavelengths, the light emitting units 31, 32, and 41 can be configured with one or more of such elements. Also, the number and the emitting wavelength of the light emitting element to be used in the light emitting units 31, 32, and 41 can be selected appropriately depending on the image to be obtained.

The light guiding member that functions as the first light source 11 has a directivity such that the light that has entered from the light emitting unit 31 arranged on the side thereof is scattered uniformly inside the first light source 11, and thereafter exits in two directions so as to reach the first light condenser lens 13 and the second light condenser lens 23. The light guiding member that functions as the third light source 12 has a directivity such that the light that has entered from the light emitting unit 32 arranged on the side thereof is scattered uniformly inside thereof, and thereafter exits in an obliquely downward direction so as to reach the first light condenser lens 13.

The light guiding members that function as the second light source 21 and the fourth light source 22 have a directivity such that the light that has entered from the light emitting units 41 arranged on the sides thereof is similarly scattered uniformly inside thereof, and thereafter exits in an upward direction so as to reach the second light condenser lens 23.

Regarding the light guiding member that changes the direction of exit of the light that has entered from a side thereof like the third light source 12, the second light source 21, and the fourth light source 22, because the technique disclosed in Japanese Patent Application Laid-open No. 2010-267524, for example, can be used, the detailed explanation thereof will be omitted.

Regarding the light guiding member that changes into two different directions the direction of exit of the light that has entered from a side thereof like the first light source 11, because the technique disclosed in Japanese Patent Application Laid-open No. 2008-216409, for example, can be used, the detailed explanation thereof will be omitted.

The first light receiving sensor 14 and the second light receiving sensor 24 are image sensors in which a plurality of elements, such as CCDs (Charge-Coupled Devices) or CMOSs (Complementary Metal Oxide Semiconductors), are arranged on a line in the Y-axis direction, and they have a function of receiving the light that is reflected from the paper sheet 100 or the light that has passed through the paper sheet 100 and outputting line data that is used to form a paper sheet image. The first light receiving sensor 14 is arranged on the first substrate 15 and the second light receiving sensor 24 is arranged on the second substrate 25.

The first substrate 15 includes a driving circuit for driving the first light receiving sensor 14, and a signal processing circuit for processing a signal outputted from the first light receiving sensor 14. The second substrate 25 includes a driving circuit for driving the second light receiving sensor 24, and a signal processing circuit for processing a signal outputted from the second light receiving sensor 24. The first substrate 15 outputs to the sensor control/signal processing unit 40 a signal based on the light received by the first light receiving sensor 14. The second substrate 25 outputs to the sensor control/signal processing unit 40 a signal based on the light received by the second light receiving sensor 24.

The first light condenser lens 13 has a function to condense the reflected light which is reflected from the paper sheet 100 when light is emitted by the first light source 11 and the third light source 12, and propagate the condensed light onto the first light receiving sensor 14. The second light condenser lens 23 has a function to condense the transmitted light which has passed through the paper sheet 100 when light is emitted by the first light source 11, or the reflected light which is reflected from the paper sheet 100 when light is emitted by the second light source 21 and the fourth light source 22, and propagate the condensed light onto the second light receiving sensor 24.

Figure 5:
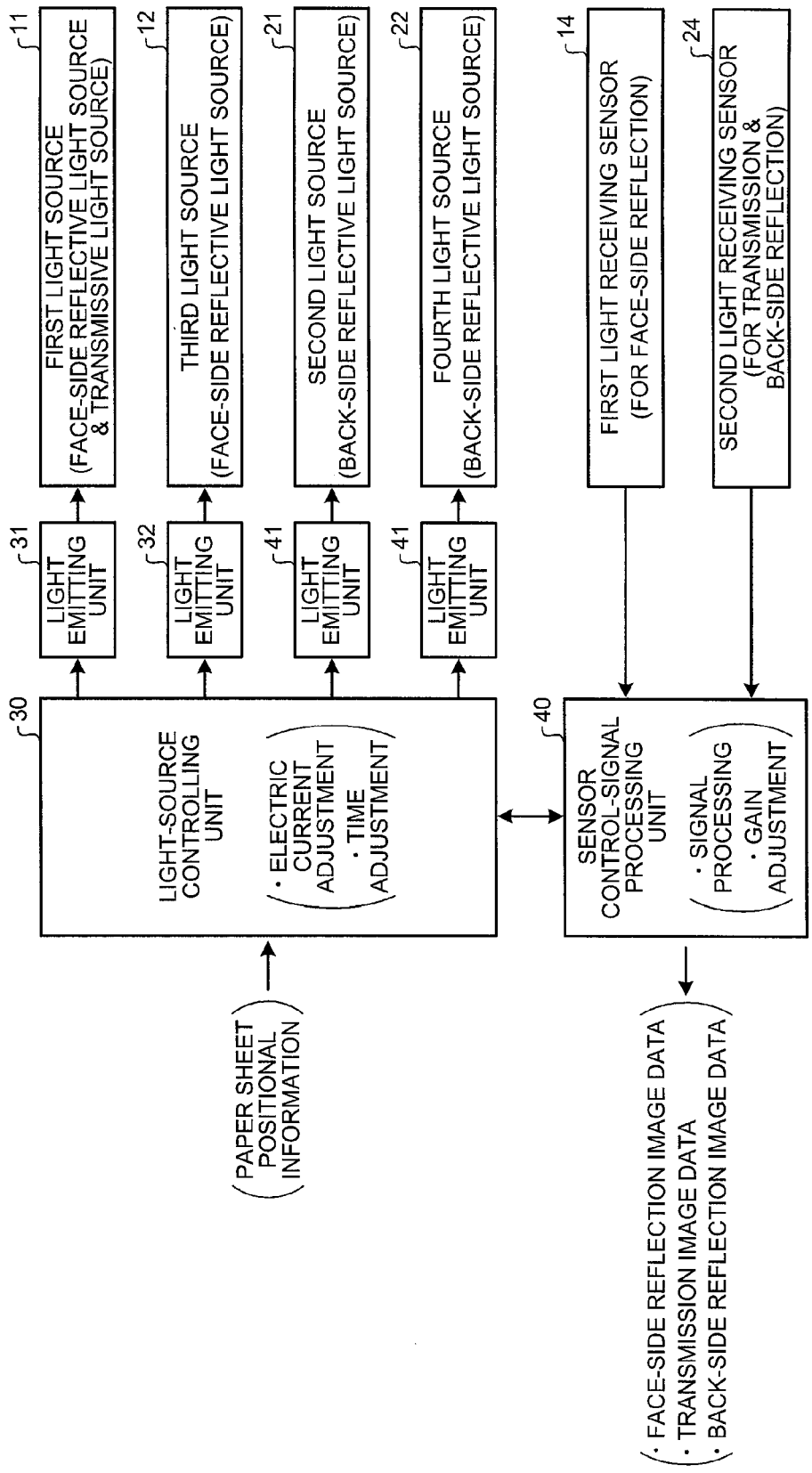
FIG. 5 is a functional block diagram for explaining a functional configuration of an image acquisition device.

Next, the functional configuration of the image acquisition device will be explained. FIG. 5 is a functional block diagram for explaining the functional configuration of the image acquisition device. As shown in FIG. 5, the light-source controlling unit 30 controls a lighting state of the light emitting units 31, 32, and 41 based on the positional information of the paper sheet 100. Specifically, the light-source controlling unit 30 controls a lighting time and a light quantity at the time of lighting by controlling on and off states and a current magnitude at the time of lighting of each of the light emitting elements 33, 34, and 43 included in the light emitting units 31, 32, and 41, respectively.

When the light emitting unit 31 emits light, the emitted light, is incident on the first light source 11, and the light is emitted on the face side of the paper sheet 100 by the first light source 11. As a result, the first light source 11 functions as a face-side reflective light source for acquiring the face-side reflection image data and a transmitted light source for acquiring the transmission image data.

When the light emitting unit 32 emits light, the emitted light is incident on the third light source 12, and the light is emitted on the face side of the paper sheet 100 by the third light source 12. As a result, the third light source 12 functions as a face-side reflective light source for acquiring the face-side reflection image data.

When the light emitting units 41 emit lights, the emitted lights are incident on the second light source 21 and the fourth light source 22, respectively, and the lights are emitted on the back side of the paper sheet 100 from the second light source 21 and the fourth light source 22. As a result, the second light source 21 and the fourth light source 22 function as back-side reflective light sources for acquiring the back-side reflection image data.

When the first light receiving sensor 14 receives the reflected light reflected from the face side of the paper sheet 100, it accumulates an electric charge corresponding to the received light quantity. Similarly, when the second light receiving sensor 24 receives the reflected light reflected from the back side of the paper sheet 100 or the transmitted light passed through the paper sheet 100, it accumulates an electric charge corresponding to the received light quantity.

The sensor control/signal processing unit 40 reads the electric charges accumulated in the first light receiving sensor 14 and the second light receiving sensor 24 as the outputs of the first light receiving sensor 14 and the second light receiving sensor 24, subjects the read outputs to signal processing and amplification, and generates the face-side reflection image data, the transmission image data, and the back-side reflection image data.

Figure 6:
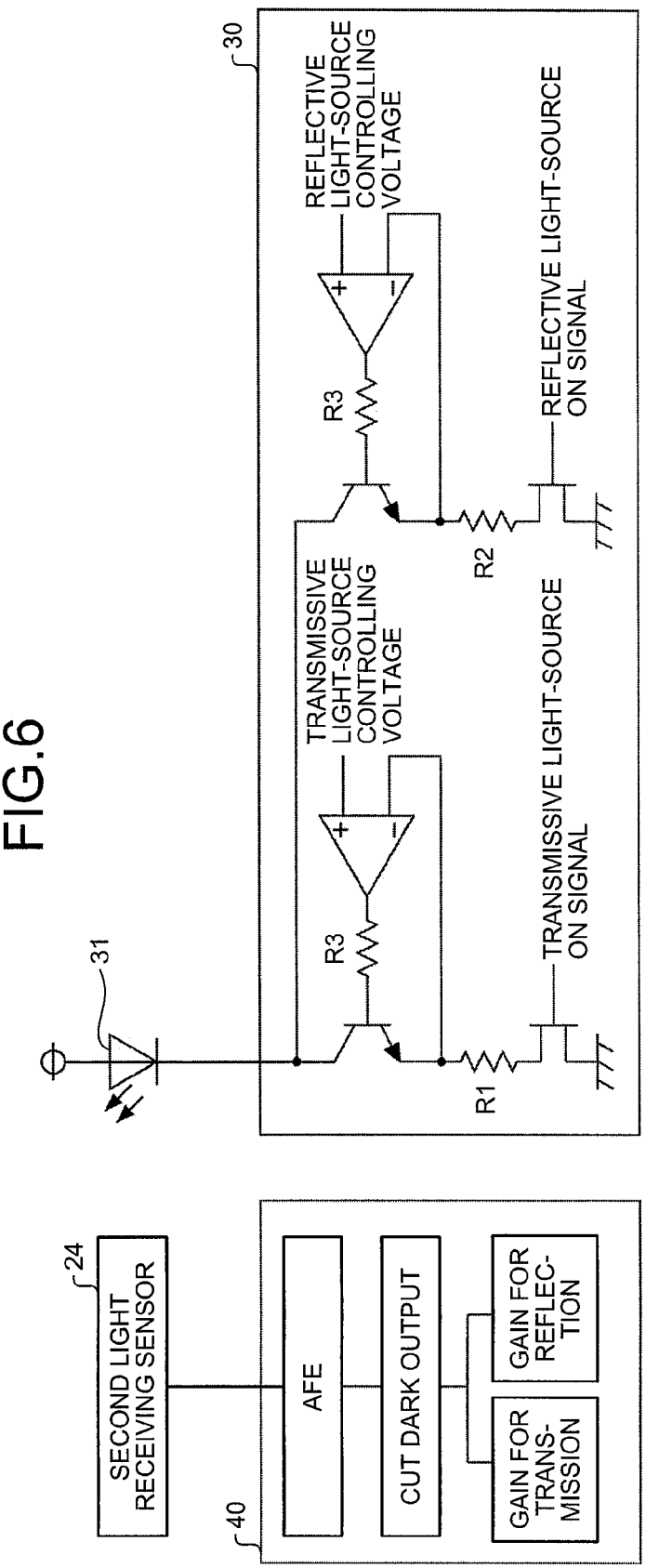
FIG. 6 is a circuit diagram for explaining a light-source controlling unit and a sensor control/signal processing unit.

Next, the light-source controlling unit 30 and the sensor control/signal processing unit 40 will be explained in detail. FIG. 6 is a circuit diagram for explaining the light-source controlling unit 30 and the sensor control/signal processing unit 40. As shown in FIG. 6, the light-source controlling unit 30 includes one operational amplifier that takes a transmissive light-source controlling voltage as the non-inverting input and another operational amplifier that takes a reflective light source controlling voltage as the non-inverting input.

The output of the operational amplifier that takes the transmissive light-source controlling voltage as the non-inverting input is connected to a base of an NPN transistor via a resistance element having a resistance value R3. A collector of this NPN transistor is connected to the light emitting unit 31 of the first light source 11. An emitter of this NPN transistor is connected to the inverting input of the operational amplifier and also connected to the ground via a resistance element having a resistance value R1 and a switch. This switch is turned on when a transmissive light-source ON signal is inputted.

The output of the operational amplifier that takes the reflective light source controlling voltage as the non-inverting input is connected to a base of an NPN transistor via a resistance element having a resistance value R3. A collector of this NPN transistor is connected to the light emitting unit 31 of the first light source 11. An emitter of this NPN transistor is connected to the non-inverting input of the operational amplifier and also connected to the ground via a resistance element having a resistance value R2 and a switch. This switch is turned on when a reflective light-source ON signal is inputted.

The reflective light-source ON signal is not inputted in a transmissive light-source ON state in which the transmissive light-source ON signal is inputted. Moreover, the transmissive light-source ON signal is not inputted in a reflective light-source ON state in which the reflective light-source ON signal is inputted.

With such a configuration and control, in the transmissive light-source ON state, a current value of a light emission current supplied to the light emitting unit 31 is fixed based on the transmissive light-source controlling voltage and the resistance value R1; and in the reflective light-source ON state, a current value of a light emission current supplied to the light emitting unit 31 is fixed based on the reflective light-source controlling voltage and resistance value R2. Specifically, the light emission current in the transmissive light-source ON state becomes substantially equal to a value obtained by dividing the transmissive light-source controlling voltage by the resistance value R1, and the light emission current in the reflective light-source ON state becomes substantially equal to a value obtained by dividing the reflective light-source controlling voltage by the resistance value R2.

Therefore, by appropriately setting the transmissive light-source controlling voltage, the resistance value R1, the reflective light-source controlling voltage, and the resistance value R2, the current values of the light emission currents supplied to the light emitting unit 31 in the transmissive light signal ON state and the reflective light signal ON state can be adjusted. Because the brightness of the light emitting unit 31 depends on the current value of the light emission current, the brightness of the light emitting unit 31 can be changed between the transmissive light signal ON state and the reflective light signal ON state by setting the current values of the light emission current to different values.

Because the light emitting units 32 and 41 are used only as the reflective light source, an operational amplifier that takes the transmissive light-source controlling voltage as the non-inverting input and various elements connected to this operational amplifier become unnecessary. Accordingly, an operational amplifier that takes the reflected light voltage as the non-inverting input and various elements connected to this operational amplifier are only used.

The sensor control/signal processing unit 40 converts the output of the second light receiving sensor 24 into a digital value by using an AFE (Analog Front End), and amplifies the digital value after cutting a dark output thereof. A gain for transmission image is used when in the transmissive light-source ON state and a gain for reflection image is used when in the reflective light-source ON state as an amplification factor for performing the amplification. A satisfactory transmission image data can be obtained by setting the gain for transmission image higher than the gain for reflection image. Because the first light receiving sensor 14 is used only for the generation of the face-side reflection image data, the gain for reflection image is always used for the output of the first light receiving sensor 14.

Next, a modification example of the light-source controlling unit 30 will be explained. FIG. 7 is an explanatory diagram for explaining the modification example of the light-source controlling unit 30. In the exemplary configuration shown in FIG. 6, two operational amplifiers, one operational amplifier that takes the transmissive light-source controlling voltage as the non-inverting input and another operational amplifier that takes the reflective light-source controlling voltage as the non-inverting input, have been used. However, it is possible to use only one operational amplifier. When only one operational amplifier is used, by varying the input thereof, the values of the light emission currents supplied to the light emitting unit 31 in the transmissive light signal ON state and the reflective light signal ON state can be adjusted.

Figure 7A:
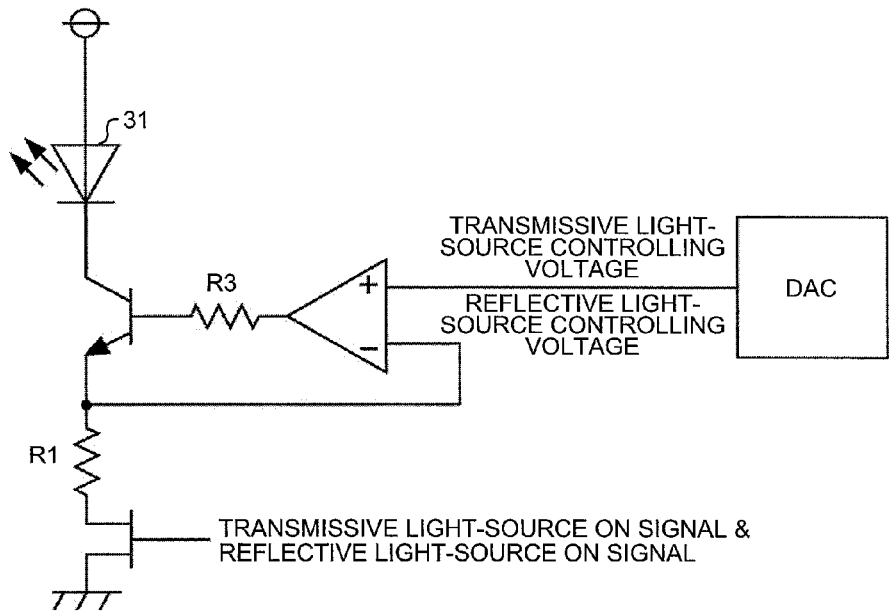
FIG. 7 is a circuit diagram for explaining a modification example of the light-source controlling unit.

In the modification example shown in FIG. 7A, an output of a DAC (Digital to Analog Converter) is supplied as the non-inverting input of the operational amplifier. Moreover, the output of the operational amplifier is connected to a base of an NPN transistor via a resistance element having a resistance value R3. A collector of this NPN transistor is connected to the light emitting unit 31 of the first light source 11. An emitter of this NPN transistor is connected to the inverting input of the operational amplifier and also connected to the ground via a resistance element having a resistance value R1 and a switch. This switch is turned on when any one of the transmissive light-source ON signal and the reflective light-source ON signal is inputted.

In the configuration shown in FIG. 7A, the DAC is controlled so that the output of the DAC becomes the transmissive light-source controlling voltage when in the transmissive light signal ON state, and the output of the DAC becomes the reflective light-source controlling voltage when in the reflective light-source ON state. Accordingly, the values of the light emission currents supplied to the light emitting unit 31 in the transmissive light signal ON state and the reflective light signal ON state can be adjusted.

Figure 7B:
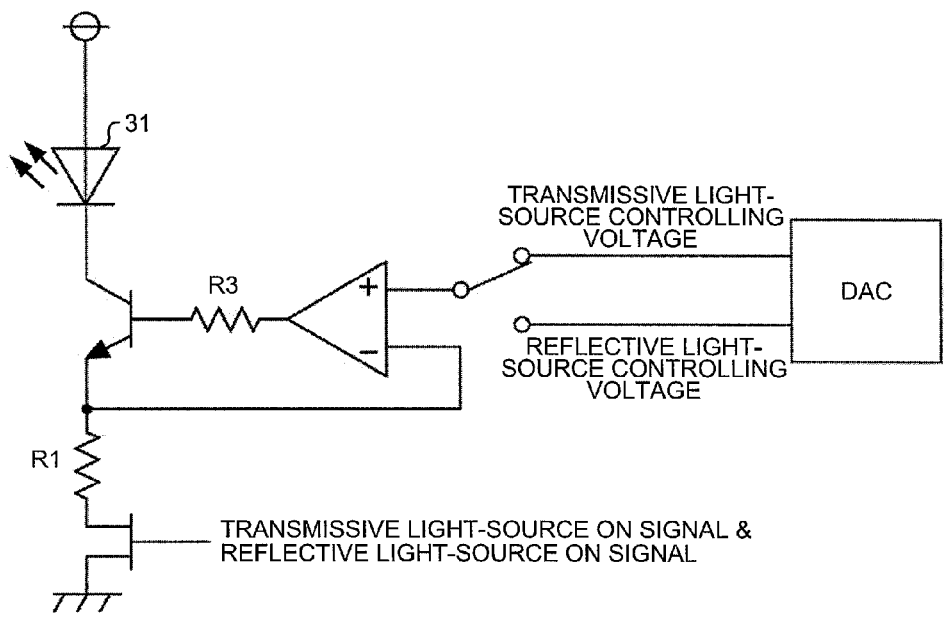

FIG. 7B shows a modification example in which a DAC outputs both the transmissive light-source controlling voltage and the reflective light-source controlling voltage, and a switch is arranged so as to select one of these two outputs and supply the selected output to the non-inverting input of the operational amplifier. The other configuration is similar to the configuration of the modification example shown in FIG. 7A. In the configuration shown in FIG. 7B, because a waiting time required for changing an output voltage by the DAC is unnecessary, switching between the transmissive light signal ON state and the reflective light signal ON state can be performed speedily.

Figure 8:
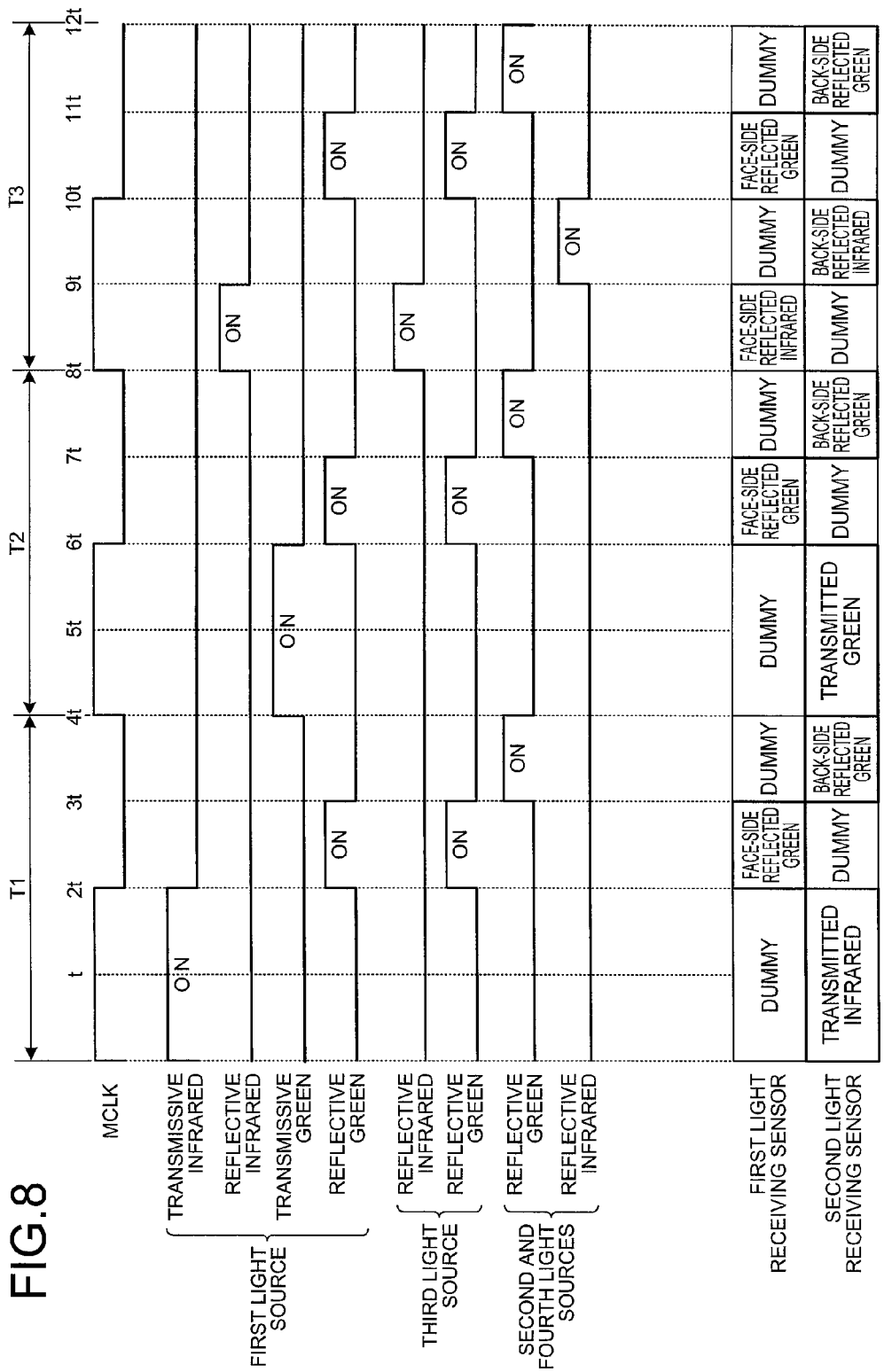
FIG. 8 is an explanatory diagram for explaining a concrete example of an operation of the image acquisition device.

Next, a concrete example of an operation of the image acquisition device will be explained. FIG. 8 is an explanatory diagram for explaining the concrete example of the operation of the image acquisition device. In the operation shown in FIG. 8, when a unit time is "t", the image acquisition device takes a clock signal MCLK of cycle T=4t as a reference and repeats the operation for T1 to T3 (=12t).

The light-source controlling unit 30 controls the first light source 11 to set transmissive infrared light ON (transmissive light source for the infrared light is ON) from a time point 0t to a time point 2t, and set transmissive infrared light OFF from the time point 2t to a time point 12t. Moreover, the light-source controlling unit 30 controls the first light source 11 to set transmissive green light OFF (transmissive light source for the green visible light is OFF) from the time point 0t to a time point 4t, set transmissive green light ON from the time point 4t to a time point 6t, and set the transmissive green light OFF from the time point 6t to the time point 12t.

The light-source controlling unit 30 controls the first light source 11 to set reflective infrared light ON (reflective light source for the infrared light is ON) from a time point 8t to a time point 9t, and set reflective infrared light OFF at any other time point. Moreover, the light-source controlling unit 30 controls the first light source 11 to set reflective green light ON (reflective light source for the green visible light is ON) from the time point 2t to a time point 3t, from the time point 6t to a time point 7t, and from a time point 10t to a time point 11t, and set reflective green light OFF at any other time point.

Similarly, the light-source controlling unit 30 controls the third light source 12 to set the reflective infrared light ON (reflective light source for the infrared light is ON) from the time point 8t to the time point 9t, and set the reflective infrared light OFF at any other time point. Moreover, the light-source controlling unit 30 controls the third light source 12 to set the reflective green light ON (reflective light source for the green visible light is ON) from the time point 2t to the time point 3t, from the time point 6t to the time point 7t, and from the time point 10t to the time point 11t, and set the reflective green light OFF at any other time point. With regard to the first light source 11, one and the same infrared LED is turned on at the time of the transmissive infrared light ON and the reflective infrared light ON, however, as explained above, different light emission currents are supplied to the LED in those two states.

Moreover, the light-source controlling unit 30 controls the second light source 21 and the fourth light source 22 to set the reflective green light ON (reflective light source for the green visible light is ON) from the time point 3t to the time point 4t, from the time point 7t to the time point 8t, and from the time point 11t to the time point 12t, and set the reflective green light OFF at any other time point. Furthermore, the light-source controlling unit 30 controls the second light source 21 and the fourth light source 22 to set the reflective infrared light ON (reflective light source for the infrared light is ON) from the time point 9t to the time point 10t, and set the reflective infrared light OFF at any other time point.

With this control, the first light source 11 is turned on as a transmissive infrared light source (transmissive light source for the infrared light) from the time point 0t to the time point 2t, turned on as a reflective green light source (reflective light source for the green visible light) from the time point 2t to the time point 3t, turned off from the time point 3t to the time point 4t, turned on as a transmissive green light source (transmissive light source for the green visible light) from the time point 4t to the time point 6t, turned on as the reflective green light source from the time point 6t to the time point 7t, turned off from the time point 7t to the time point 8t, turned on as a reflective infrared light source (reflective light source for the infrared light) from the time point 8t to the time point 9t, turned off from the time point 9t to the time point 10t, turned on as the reflective green light source from the time point 10t to the time point 11t, and turned off from the time point 11t to the time point 12t.

The third light source 12 is turned on as the reflective green light source from the time point 2t to the time point 3t, turned on as the reflective green light source from the time point 6t to the time point 7t, turned on as the reflective infrared light source from the time point 8t to the time point 9t, and turned on as the reflective green light source from the time point 10t to the time point 11t. The third light source 12, when used as a reflective light source above the transport path, is always turned on or off simultaneously with the first light source 11.

The second light source 21 and the fourth light source 22 are turned on as the reflective green light source from the time point 3t to the time point 4t, turned on as the reflective green light source from the time point 7t to the time point 8t, turned on as the reflective infrared light source from the time point 9t to the time point 10t, turned on as the reflective green light source from the time point 11t to the time point 12t, and turned off at any other time point.

The first light receiving sensor 14 receives face-side reflected green light (the green visible light reflected from the face side of the paper sheet 100) from the time point 2t to the time point 3t, accumulates an electric charge, and the accumulated electric charge is read. The first light receiving sensor 14 receives the face-side reflected green light from the time point 6t to the time point 7t, accumulates an electric charge, and the accumulated electric charge is read. The first light receiving sensor 14 receives face-side reflected infrared light (the infrared light reflected from the face side of the paper sheet 100) from the time point 8t to the time point 9t, and accumulates an electric charge. The first light receiving sensor 14 receives the face-side reflected green light from the time point 10t to the time point 11t, and accumulates an electric charge. Dummy reading is performed at time points other that those mentioned here, but the read data is not used for the generation of the image data.

The second light receiving sensor 24 receives transmitted infrared light (the infrared light that has passed through the paper sheet 100) from the time point 0t to the time point 2t, accumulates electric charge, and the accumulated electric charge is read. The second light receiving sensor 24 receives back-side reflected green light (the green visible light reflected from the back side of the paper sheet 100) from the time point 3t to the time point 4t, accumulates electric charge, and the accumulated electric charge is read. The second light receiving sensor 24 receives transmitted green light (the green visible light that has passed through the paper sheet 100) from the time point 4t to the time point 6t, accumulates an electric charge, and the accumulated electric charge is read. The second light receiving sensor 24 receives the back-side reflected green light from the time point 7t to the time point 8t, accumulates electric charge, and the accumulated electric charge is read. The second light receiving sensor 24 receives back-side reflected infrared light (the infrared light reflected from the back side of the paper sheet 100) from the time point 9t to the time point 10t, accumulates electric charge, and the accumulated electric charge is read. The second light receiving sensor 24 receives the back-side reflected green light from the time point 11t to the time point 12t, and accumulates electric charge. Dummy reading is performed at time points other that those mentioned here, but the read data is not used for the generation of the image data.

In this manner, in the operation shown in FIG. 8, because time for each of the light reception and the light emission for the reflected light is set to 1t in contrast to 2t for the same for the transmitted light, sufficient electric charge can be accumulated even when the second light receiving sensor 24 receives the transmitted light, and satisfactory output can be obtained.

Because the light reception and the light emission are performed while the paper sheet 100 is being transported, the cycle of the light reception and the light emission influences the resolution of the acquired image data. The reason why the light reception and the light emission are performed for every 12t for the reflective infrared light, whereas the same is performed for every 4t for the reflective green light, is because the resolution necessary to recognize the paper sheet varies according to wavelengths.

In the operation example shown in FIG. 8, a case is explained in which the light reception and the light emission are performed separately for generating each of the face-side reflection image data and the transmission image data; however, the light reception for generating the transmission image data can be performed simultaneously with the light reception and the light emission performed for the generation of the face-side reflection image data.

By performing the light reception for generating the transmission image data simultaneously with the light reception and the light emission performed for the generation of the face-side reflection image data, the face-side reflection image data and the transmission image data can be acquired simultaneously.

FIG. 9 is an explanatory diagram for explaining a concrete example of an operation of the image acquisition device when performing such simultaneous acquiring. In the operation shown in FIG. 9, when a unit time is "t", the image acquisition device takes a clock signal MCLK of period T=5t as a reference and repeats the operation for T1 to T2 (=10t).

The light-source controlling unit 30 controls the first light source 11 to set transmissive/reflective infrared light ON from a time point 0t to a time point 2t, and set transmissive/reflective infrared light OFF from the time point 2t to a time point 5t. Moreover, the light-source controlling unit 30 controls the first light source 11 to set the transmissive/reflective infrared light ON from the time point 5t to a time point 6t, and set the transmissive/reflective infrared light OFF from the time point 6t to a time point 10t. Moreover, the light-source controlling unit 30 controls the first light source 11 to set transmissive/reflective green light OFF from the time point 0t to a time point 3t, and set transmissive/reflective green light ON from the time point 3t to a time point 4t. Moreover, the light-source controlling unit 30 controls the first light source 11 to set the transmissive/reflective green light OFF from the time point 4t to a time point 7t, set the transmissive/reflective green light ON from the time point 7t to a time point 9t, and set the transmissive/reflective green light OFF from the time point 9t to the time point 10t.

The light-source controlling unit 30 controls the third light source 12 to set the reflective infrared light ON from the time point 0t to a time point 1t, set the reflective infrared light ON from the time point 5t to the time point 6t, and set the reflective infrared light OFF at any other time point. The light-source controlling unit 30 controls the third light source 12 to set the reflective green light ON from the time point 3t to the time point 4t, set the reflective green light ON from the time point 7t to a time point 8t, and set the reflective green light OFF at any other time point.

Moreover, the light-source controlling unit 30 controls the second light source 21 and the fourth light source 22 to set the reflective green light ON from the time point 4t to the time point 5t and from the time point 9t to the time point 10t, and set the reflective green light OFF at any other time point. Furthermore, the light-source controlling unit 30 controls the second light source 21 and the fourth light source 22 to set the reflective infrared light ON from the time point 2t to the time point 3t and from the time point 6t to the time point 7t, and set the reflective infrared light OFF at any other time point. In the embodiment shown in FIG. 9, the first light source 11 and the third light source 12 are always turned on or off simultaneously while emitting the lights having the same wavelength.

With this control, the first light source 11 is turned on to function both as the transmissive infrared light source and as the reflective infrared light source from the time point 0t to the time point 2t, turned off from the time point 2t to the time point 3t, turned on as the reflective green light source from the time point 3t to the time point 4t, turned off from the time point 4t to the time point 5t, turned on as the reflective infrared light source from the time point 5t to the time point 6t, turned off from the time point 6t to the time point 7t, turned on to function both as the transmissive green light source and as the reflective green light source from the time point 7t to the time point 9t, and turned off from the time point 9t to the time point 10t.

The third light source 12 is turned on as the reflective infrared light source from the time point 0t to the time point 1t, turned on as the reflective green light source from the time point 3t to the time point 4t, turned on as the reflective infrared light source from the time point 5t to the time point 6t, turned on as the reflective green light source from the time point 7t to the time point 8t, and turned off at any other time point.

The second light source 21 and the fourth light source 22 are turned on as the reflective infrared light source from the time point 2t to the time point 3t, turned on as the reflective green light source from the time point 4t to the time point 5t, turned on as the reflective infrared light source from the time point 6t to the time point 7t, turned on as the reflective green light source from the time point 9t to the time point 10t, and turned off at any other time point.

The first light receiving sensor 14 receives the face-side reflected infrared light from the time point 0t to the time point t, accumulates electric charge, and the accumulated electric charge is read. The first light receiving sensor 14 receives the face-side reflected green light from the time point 3t to the time point 4t, accumulates electric charge, and the accumulated electric charge is read. The first light receiving sensor 14 receives the face-side reflected infrared light from the time point 5t to the time point 6t, accumulates electric charge, and the accumulated electric charge is read. The first light receiving sensor 14 receives the face-side reflected green light from the time point 7t to the time point 8t, accumulates electric charge, and the accumulated electric charge is read. Dummy reading is performed at time points other that those mentioned here, but the read data is not used for the generation of the image data.

The second light receiving sensor 24 receives the transmitted infrared light from the time point 0t to the time point 2t, accumulates electric charge, and the accumulated electric charge is read. The second light receiving sensor 24 receives the back-side reflected infrared light from the time point 2t to the time point 3t, accumulates electric charge, and the accumulated electric charge is read. The second light receiving sensor 24 receives the back-side reflected green light from the time point 4t to the time point 5t, accumulates electric charge, and the accumulated electric charge is read. The second light receiving sensor 24 receives the back-side reflected infrared light from the time point 6t to the time point 7t, accumulates electric charge, and the accumulated electric charge is read. The second light receiving sensor 24 receives the transmitted green light from the time point 7t to the time point 9t, accumulates an electric charge, and the accumulated electric charge is read. The second light receiving sensor 24 receives the back-side reflected green light from the time point 9t to the time point 10t, accumulates electric charge, and the accumulated electric charge is read. Dummy reading is performed at time points other that those mentioned here, but the read data is not used for the generation of the image data.

In this manner, in the operation shown in FIG. 9, because acquiring of the face-side reflected light and the transmitted light is performed simultaneously from the time point 0t to the time point t and from the time point 7t to the time point 8t, the face-side reflection image data, the back-side reflection image data, and the transmission image data can be acquired by repeating the operation for 10t. Therefore, realization of improvement of the resolution becomes possible in comparison of a case shown in FIG. 8 where the operation is repeated for 12t.

As explained above, in the image acquisition device according to the present embodiment, because the first light source 11 is used in common for the generation of the face-side reflection image data and the generation of the transmission image data, and the second light receiving sensor 24 is used in common for the generation of the back-side reflection image data and the generation of the transmission image data, the face-side reflection image data, the transmission image data, and the back-side reflection image data can be obtained with a small and low-cost device configuration. In this manner, if downsizing of the image acquisition device can be realized, the empty space that became available by the downsizing can be used to arrange driving members for transporting the paper sheet 100, whereby the paper sheet 100 can be transported stably.

In the image acquisition device according to the present embodiment, the brightness of the first light source 11, the lighting time of the first light source 11, the accumulation time in which optical charge is accumulated in the second light receiving sensor 24, a reading time in which output signal is read from the second light receiving sensor 24, and the amplification factor by which the output of the second light receiving sensor 24 is amplified are controlled by taking into account the directivity of the first light source 11 in two directions, and thus the light quantity necessary for the generation of satisfactory transmission image data can be acquired.

The configuration and the operation disclosed in the present embodiment is not intended to limit the present invention, and the configuration and the operation can be appropriately changed and implemented. For example, it is allowable to employ a configuration in which the number of the LEDs turned on is changed in the case of generating the reflection image data and in the case of generating the transmission image data thereby realizing appropriate light quantity for the generation of their respective image data. Moreover, the lighting time of each of the light sources, the accumulation time of each of the light receiving sensors, and the like can be set different for every wavelength.

In the present embodiment, an example is explained in which the infrared light and the green visible light is used;

however, the present invention can be similarly applied even when the lights from the ultraviolet to the infrared band are used.

INDUSTRIAL APPLICABILITY

As explained above, the image acquisition device and the image acquisition method according to the present invention are suitable for acquiring satisfactory reflection image and transmission image of the paper sheet while realizing the downsizing of the device.

EXPLANATION OF REFERENCE NUMERALS 10, 20 Light receiving/emitting unit
11 First light source
12 Third light source
13 First light condenser lens
14 First light receiving sensor
15 First substrate
16, 26 Transparent member
17, 27 Housing
21 Second light source
22 Fourth light source
23 Second light condenser lens
24 Second light receiving sensor
25 Second substrate
30 Light-source controlling unit
31, 32, 41 Light emitting unit
33, 34, 43 Light emitting element
40 Sensor control/signal processing unit
100 Paper sheet

The invention claimed is:

1. An image acquisition device that acquires image data of a paper sheet being transported on a transport path, comprising:
   a first light source arranged on one side of the paper sheet being transported on the transport path;
   a first light receiving sensor that receives a reflected light that is emitted by the first light source and reflected from the paper sheet being transported; and
   a second light receiving sensor that is arranged on other side of the paper sheet being transported on the transport path and receives a transmitted light that has passed through the paper sheet being transported,
   wherein the first light source outputs a light having directivity in both directions of a first direction for supplying the reflected light reflected from the paper sheet to the first light receiving sensor and a second direction for supplying the transmitted light passed through the paper sheet to the second light receiving sensor,
   the first light source emits a predetermined light quantity by dividing in the first direction and the second direction, and
   a division ratio of light quantity to be emitted in the second direction is higher than a division ratio of the light quantity to be emitted in the first direction.

2. The image acquisition device according to claim 1, further comprising a second light source arranged on the other side on which the second light receiving sensor is arranged, wherein
   the first light receiving sensor receives a first reflected light that is emitted by the first light source and reflected from the one side of the paper sheet, and
   the second light receiving sensor receives a second reflected light that is emitted by the second light source and reflected from the other side of the paper sheet, and receives the transmitted light that is emitted by the first light source and passed through the paper sheet.

3. The image acquisition device according to claim 2, further comprising:
   a third light source arranged on the same side as the first light receiving sensor, the first light source and the third light source being arranged in each of front and back of the first light receiving sensor; and
   a second light source and a fourth light source arranged on the same side as the second light receiving sensor, the second light source and the fourth light source being arranged in each of front and back of the second light receiving sensor.

4. The image acquisition device according to claim 2, wherein a lighting time of the first light source when the second light receiving sensor receives the transmitted light is longer than one or both of
   a lighting time of the first light source when the first light receiving sensor receives the reflected light reflected from the paper sheet being transported and a lighting time of the second light source when the second light receiving sensor receives the reflected light reflected from the paper sheet being transported.

5. The image acquisition device according to claim 2, wherein a light emission current supplied to the first light source when the second light receiving sensor receives the transmitted light is larger than one or both of
   a light emission current supplied to the first light source when the first light receiving sensor receives the reflected light reflected from the paper sheet being transported and a light emission current supplied to the second light source when the second light receiving sensor receives the reflected light reflected from the paper sheet being transported.

6. The image acquisition device according to claim 2, wherein
   one or both of the first light source and the second light source performs light emission of different wavelengths in a time division manner, and
   at least one among
      a lighting time of one or both of the first light source and the second light source,
      a light emission current to be supplied to one or both of the first light source and the second light source,
      an accumulation time of the first light receiving sensor and the second light receiving sensor, and
      an amplification factor for amplifying an output of the first light receiving sensor and the second light receiving sensor,
   are changed based on the wavelength.

7. The image acquisition device according to claim 1, wherein the first light source is a line-shaped light source.

8. The image acquisition device according to claim 1, wherein an accumulation time for accumulating optical charge in the second light receiving sensor when receiving the transmitted light is longer than one or both of
   an accumulation time for accumulating optical charge in the first light receiving sensor when receiving the reflected light reflected from the paper sheet being transported and an accumulation time for accumulating optical charge in the second light receiving sensor when receiving the reflected light reflected from the paper sheet being transported.

9. The image acquisition device according to claim 1, wherein an amplification factor by which an output of the second light receiving sensor is amplified when the second light receiving sensor receives the transmitted light is higher than one or both of
- an amplification factor by which an output of the first light receiving sensor is amplified when the first light receiving sensor receives the reflected light reflected from the paper sheet being transported and an amplification factor by which an output of the second light receiving sensor is amplified when the second light receiving sensor receives the reflected light reflected from the paper sheet being transported.

10. The image acquisition device according to claim 1, wherein light reception by the first light receiving sensor of the reflected light from the paper sheet being transported and light reception by the second light receiving sensor of the transmitted light are performed simultaneously.

11. An image acquisition method of acquiring image data of a paper sheet being transported on a transport path, comprising:
- a first emission step in which a first light source, arranged on one side of the paper sheet being transported on the transport path, emits a light having a directivity in both directions of a first direction for supplying a light so that a reflected light that has reflected from one side of the paper sheet is received by a first light receiving sensor and a second direction for supplying a light so that a transmitted light that has passed through the paper sheet is received by a second light receiving sensor arranged on other side of the transport path;
- a first reflected light receiving step in which the first light receiving sensor receives a first reflected light emitted by the first light source and reflected from the one side of the paper sheet; and
- a transmitted light receiving step in which the second light receiving sensor receives a transmitted light emitted by the first light source and that has passed through the paper sheet
- wherein the first light source emits a predetermined light quantity by dividing in the first direction and the second direction, and,
- a division ratio of the light quantity to be emitted in the second direction is higher than a division ratio of the light quantity to be emitted in the first direction.

* * * * *